United States Patent [19]

Brown et al.

[11] Patent Number: 5,566,821

[45] Date of Patent: Oct. 22, 1996

[54] SUTURE RETAINER

[75] Inventors: David L. Brown, Wallingford, Conn.;
Andrew P. Stellon, Rivervlae, N.J.;
Edward A. Gemma, Jr., Milford, Conn.

[73] Assignee: United States Surgical Corporation, Norwalk, Conn.

[21] Appl. No.: 370,956

[22] Filed: Jan. 10, 1995

[51] Int. Cl.⁶ ................................................ A61B 17/04
[52] U.S. Cl. ........................................ 206/63.3; 206/388
[58] Field of Search ................................ 206/63.3, 388, 206/227, 382, 380

[56] References Cited

U.S. PATENT DOCUMENTS

| | | |
|---|---|---|
| 693,138 | 2/1902 | Johnson ..................... 206/63.3 |
| 2,665,805 | 1/1954 | Schaefer .................... 206/63.3 |
| 3,147,861 | 9/1964 | Kurtz ........................ 206/63.3 |
| 3,857,484 | 12/1974 | Thyen . |
| 4,063,638 | 12/1977 | Marwood et al. . |
| 4,089,409 | 5/1978 | Cerwin . |
| 4,120,395 | 10/1978 | Mandel et al. . |
| 4,249,656 | 2/1981 | Cerwin et al. . |
| 4,406,363 | 9/1983 | Aday . |
| 4,427,109 | 1/1984 | Roshdy . |
| 4,483,437 | 11/1984 | Cerwin et al. . |
| 4,491,218 | 1/1985 | Aday . |
| 4,496,045 | 1/1985 | Ferguson et al. . |
| 4,549,649 | 10/1985 | Roshdy ..................... 206/63.3 |
| 4,555,016 | 11/1985 | Aday et al. . |
| 4,572,363 | 2/1986 | Alpern . |
| 4,574,948 | 3/1986 | Huck et al. . |
| 4,574,957 | 3/1986 | Stead . |
| 4,615,435 | 10/1986 | Alpern et al. . |
| 4,813,537 | 3/1989 | Okuhara et al. . |
| 4,884,681 | 12/1989 | Roshdy et al. . |
| 5,101,968 | 4/1992 | Henderson et al. . |
| 5,121,836 | 6/1992 | Brown et al. . |
| 5,236,082 | 8/1993 | Brown . |
| 5,277,299 | 1/1994 | Holzwarth et al. . |
| 5,425,445 | 6/1995 | Brown et al. .............. 206/63.3 |

FOREIGN PATENT DOCUMENTS

13053    8/1903    Austria ................... 206/388

Primary Examiner—Bryon P. Gehman

[57] ABSTRACT

A surgical suture retainer retains the suture in an epitrochoidal, or hourglass configuration. One embodiment includes an insert member mounted to one of several foldable connected panels of the suture retainer. The insert member preferably has first and second wings which fold over to form a suture retaining pocket. The suture is held in a looped configuration having an hourglass shape. Another embodiment employs tabs cut from one of the panels to retain the suture in the hourglass shape. Yet another embodiment employs a cover sheet bonded to a base panel, wherein bonding areas are located to maintain the suture loop in an hourglass shape.

31 Claims, 9 Drawing Sheets

SUTURE RETAINER

BACKGROUND OF THE INVENTION

1. Field of the Invention

The present invention relates to suture retainers, and more particularly to a retainer for surgical sutures with one or more needles attached thereto.

2. Background of the Art

Typical suture retainers are packages which include folded paper structure for retaining one or more sutures. The suture, can be "armed," i.e. attached to a surgical needle, or it can be "unarmed," i.e., supplied in pre-cut lengths. "Double armed" sutures are those with both ends attached to respective needles. The retainer can be sterilized and disposed in one or more hermetically sealed envelopes to maintain sterility. To use the suture, the envelopes are removed and the retainer is partially or wholly opened or otherwise manipulated to provide access to the suture and/or needle(s). The needle or suture end portion can be individually grasped with forceps and pulled from the retainer, resulting in withdrawal of the trailing suture strand.

Suture retainers are intended to protect sutures from mechanical, microbial, and chemical degradation during shipping, handling, and storage, while allowing the sutures to be removed. The suture retainer should possess good storing qualities, provide safety in handling, and permit ready access to, and removal of, the stored sutures. Removal needs to be smooth and provide a suture free of tangles and kinks.

Various types of suture retainers are known and disclosed in the art. For example, commonly assigned U.S. Pat. No. 5,121,836, herein incorporated by reference, discloses a multipanel suture retainer for an armed surgical suture. The suture retainer has a needle retaining panel, a front cover panel, a suture winding panel, and a fold over panel. Apertures for loading pins facilitate the loading of the suture in a "FIG. 8", or lemniscate type pattern. The lemniscate pattern includes a central crossover point where the suture strand crosses over itself. While this package and suture pattern has been used successfully for years, it is desirable to eliminate suture crossover points to reduce potential wear during shipment and storage.

U.S. Pat. No. 3,627,120 discloses a suture package that retains a suture coil in an oval configuration. The package has a pair of opposed, arc-shaped tabs cut in a panel. The tabs extend longitudinally and are adapted to flexibly engage and overlie the longitudinal strands of the suture coil. To remove the suture, the package is opened and the suture withdrawn.

SUMMARY OF THE INVENTION

A retainer for armed and unarmed surgical sutures is provided herein. The suture retainer advantageously holds a suture loop in an epitrochoidal (i.e. "hourglass") configuration, as opposed to a lemniscate, (i.e. "FIG. 8") configuration or an oval configuration. The hourglass configuration advantageously provides controlled and tangle free withdrawal of the suture from the package by providing frictional interference. In one embodiment, the suture retainer includes four foldably connected panels, i.e. a needle retaining panel, a front cover panel connected to the needle retaining panel, a suture winding panel connected to the front cover panel, and fold-over panel connected to the suture winding panel.

One preferred embodiment to maintain a suture in an hourglass configuration is an insert member mounted to a suture winding panel. The insert member preferably has a center portion bonded to the suture winding panel and first and second wings foldably connected to the center portion along respective fold lines, the first and second wings being foldable over the center portion so as to form a suture retaining pocket. Most preferably, the fold lines are inwardly inclined toward each other so as to form a generally V-shaped boundary. The insert is preferably fabricated from a sheet of spunbonded polyolefin fibers, such as TYVEK® brand sheet.

In an alternate embodiment, the suture can be held in an hourglass configuration by tabs cut from one or more of the panels. After loading the suture, the tabs can be folded there over. Yet another preferred embodiment employs a cover sheet bonded to a base panel wherein bonding areas are located to maintain the suture loop in the hourglass shape.

In each embodiment, the structure that maintains the suture in the "hourglass" or "epitrochoidal" shape also provides frictional interference upon withdrawal. Such interference is not present, for example, in coiled suture strands that are packaged in an "oval" configuration, wherein portions of the suture are generally disposed longitudinally in the package.

DETAILED DESCRIPTION OF PREFERRED EMBODIMENT(S)

The suture retainer of the present invention is adapted to retain a suture loop having one or more turns of suture in an epitrochoidal, or "hourglass" shape. The suture does not cross over itself as in commonly used lemniscate (i.e. "figure 8") configurations and is not disposed in an oval configuration. One or more sutures may be retained. The sutures can be single armed (one needle attached), double armed (a needle attached to each of the two ends of the suture) or unarmed (no needles attached). The suture retainer can have foldably connected panels, or a single panel with a cover sheet. The panels can be fabricated from paper stock, TYVEK® brand sheet of spunbonded polyolefin fibers, plastic sheet or any other material suitable for the purposes described herein. The suture can be a monofilament surgical suture or a braided multifilament surgical suture fabricated from a non-bioabsorbable, or bioabsorbable synthetic polymer such as homopolymers and copolymers of glycolide, lactide, p-dioxanone, caprolactone, and the like.

Figure 1:
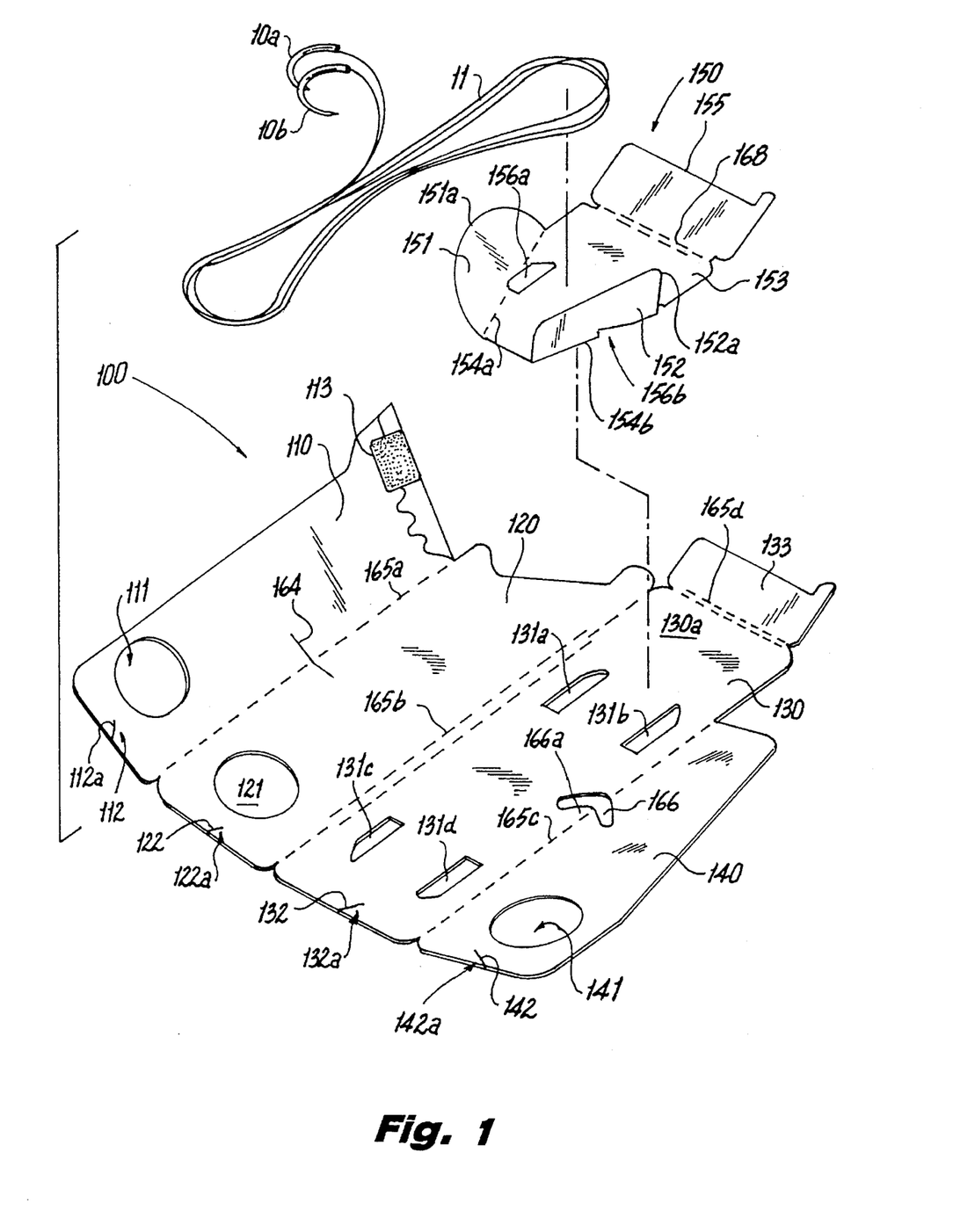
FIG. 1 is an exploded perspective view of a suture retainer having an insert for maintaining the suture in an hourglass configuration.

Turning to FIG. 1, a preferred embodiment of a folded panel suture retainer 100 is illustrated. Retainer 100 has four foldably connected panels 110, 120, 130 and is shown holding a double armed suture 11 having needles 10a and 10b attached at the ends. While a double-armed suture is shown, single armed an unarmed sutures can also be packaged in retainer 100.

Referring additionally now to FIGS. 2, 3, 4, and 6, first panel 110 is a needle retaining panel which includes needle park 113. Needle park 113 is preferably a foam block into which needles are retained. Circular cutout aperture 111 in panel 110 is a fill port which allows optional packing fluid (e.g., isopropyl alcohol) to be added to the package when the package is in the folded condition. Other fill ports, i.e. aperture 121 on panel 120, and aperture 141 on panel 140, are positioned such that all the fill ports are aligned to provide access through the panels when the suture retainer 100 is folded. Indentations 162, and 163 serve to prevent the suture from being caught between the panels when folded.

Figure 2:
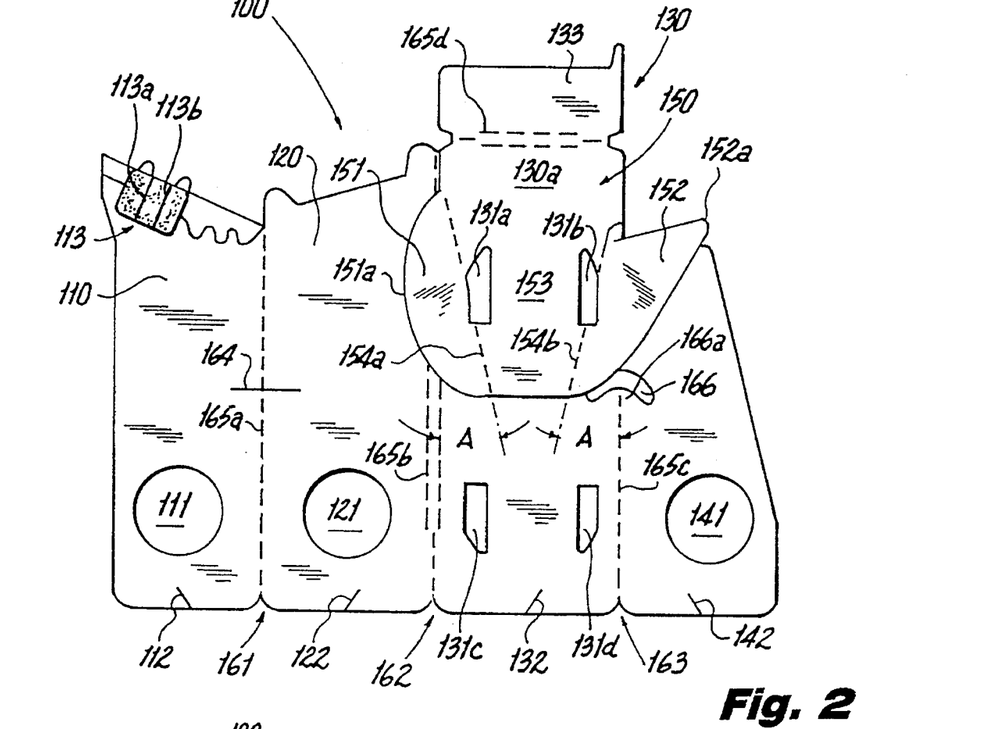
FIG. 2 is a plan view of the unfolded suture retainer of Fig. 1.

Needle retaining panel 110 is connected to front cover panel 120 via fold line 165a. Front panel 120 is connected to suture winding panel 130 via gusset 165b. Panel 130 is connected to fold over panel 140 via fold line 165c.

Panel 130 includes a main body 130a and apertures 131a, 131b, 131c, and 131d which permit loading pins to project therethrough. During the loading process the suture is wound around the loading pins. The loading pins can then be withdrawn leaving a suture loop. More details about suture loading are set forth below. Panel 130 also includes a fold over flap 133 foldably connected at the top edge of main body 130a by gusset 165d. Fold over flap 133 folds down to cover needles or suture end portions when suture retainer 100 is fully folded.

As shown, retainer 100 includes insert 150 which is fixedly attached to panel 130. Insert 150 is preferably made from a sheet composed of spun bonded polyolefin fibers, such as TYVEK® brand sheet material, and is preferably bonded to panel 130 by an adhesive or welded thereto by heat or ultra sound. Insert 150 includes center panel 153 and foldably connected wings 151 and 152. Wing 151 preferably is connected to center panel 153 at fold line 154a, wing 152 is connected to panel 153 at fold line 154b. Fold lines 154a and 154b are inclined inward at an angle A (FIG. 2) of from about 5° to about 45° from the panel fold lines, and together they define a V-shaped boundary. Thus, wings 151 and 152 provide spaced apart suture abutment surfaces generally facing each other in non-parallel relationship for contacting the outside of the suture loop. Wing 151 has a rounded edge 151a, whereas wing 152 preferably has an edge with an extended corner 152a. Upper flap 155 is foldably connected to the upper part of panel 153 at gusset 168. Apertures 156a and 156b are provided to align with corresponding apertures 131a and 131b on panel 130.

Insert 150, when folded, forms a suture loop retaining pocket. The inward angling of the fold lines imparts contraposed incurvations to the sides of the suture loop giving an epitrochoidal or "hourglass" shape to the loop of suture and facilitating smooth withdrawal of the suture.

Figures 4, 5, 6:
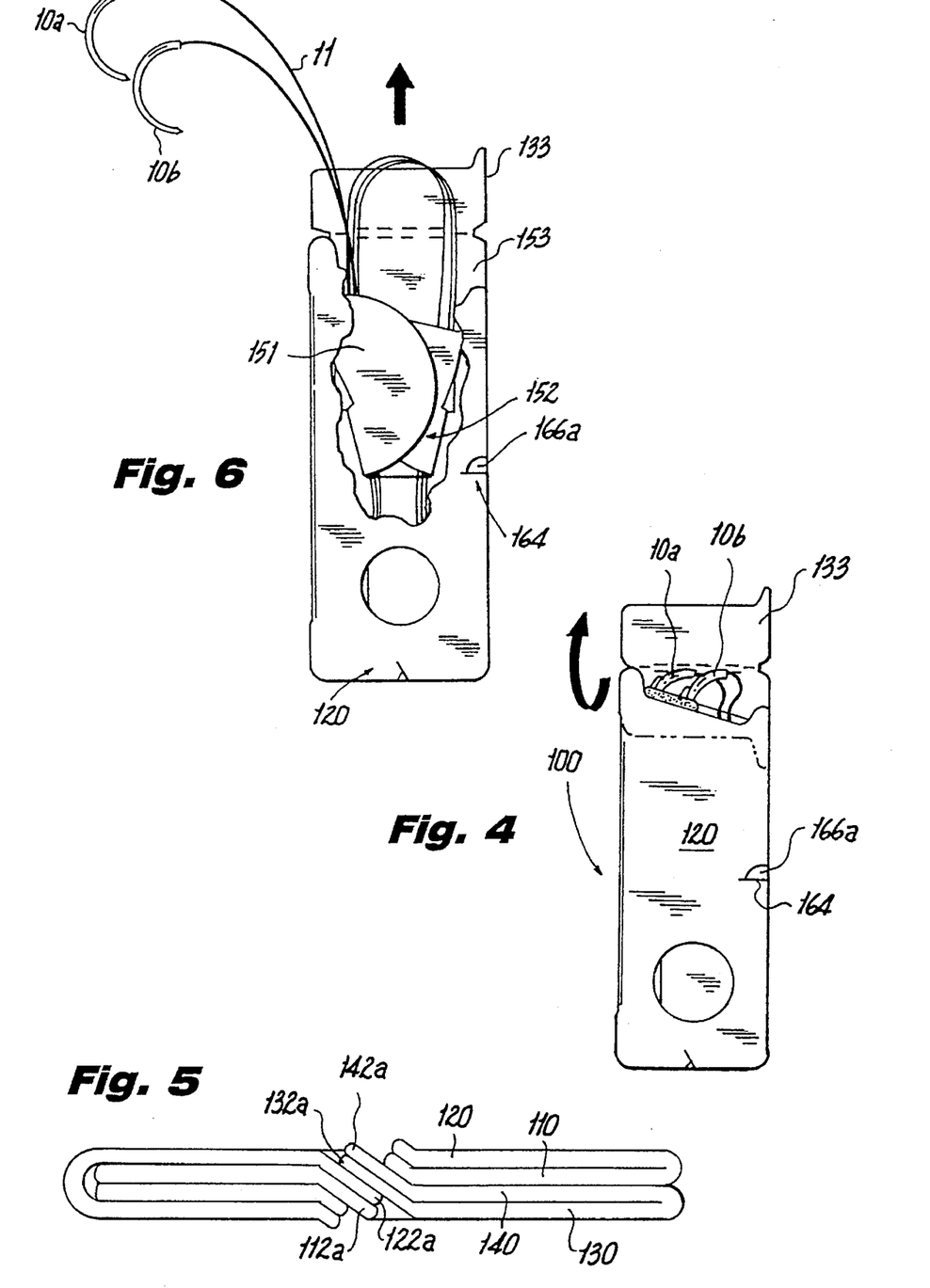
FIG. 4 is a plan view of the suture retainer of FIG. 3 after it has been closed.
FIG. 5 is an edge view showing a preferred locking feature.
FIG. 6 is a partial cutaway plan view showing removal of a double-armed suture from the retainer.

Suture retainer 100 also includes traverses fold line 165c and linear slit 164 traverses fold line 165a. The arcuate slot 166 defines a tab 166a which is insertable through slit 164 when the suture retainer 100 is completely folded as shown in FIGS. 4 and 6. Another locking mechanism is provided by slanted slits 112, 122, 132, and 142 at the bottom edges of their respective panels wherein each slit 112, 122, 132, and 142 defines respective tabs 112a, 122a, 132a, and 142a. As shown in FIG. 5, when suture retainer 100 is folded tabs 132a and 142a are aligned in one direction, whereas tabs 112a and 122a are aligned in the opposite direction. When the bottom edge locking means is engaged, tabs 142a and 132a are inserted through slits 112 and 122. Conversely, tabs 112a and 122a are inserted through slits 132 and 142. Once engaged, the combination of tabs and slits prevent inadvertent opening of suture retainer 100.

To load a suture, the winding pins are first inserted through apertures 131a, 131b, 131c, and 131d. The suture is wound around the winding pins, to form a circular or oval coil having multiple suture turns, or windings, but only a single loop rather than in a "figure 8", or lemniscate pattern, which has two loops defined by a center crossover point. The single loop winding of the present invention is easier, quicker, and requires less complicated loading machinery and operations. It is preferable for twisted sutures which have a particular "lay" or direction of twist, although any suture with or without a lay may be conveniently retained. Also, it can also be used for braided suture, especially braided sutures having a twisted core. Sutures such as those described in U.S. Pat. Nos. 5,306,289 and 5,059,213 are conveniently retained by the present invention. If the suture is armed, the needles are retained by needle receiving slits 113a and 113b in foam pad 113.

Figure 3:
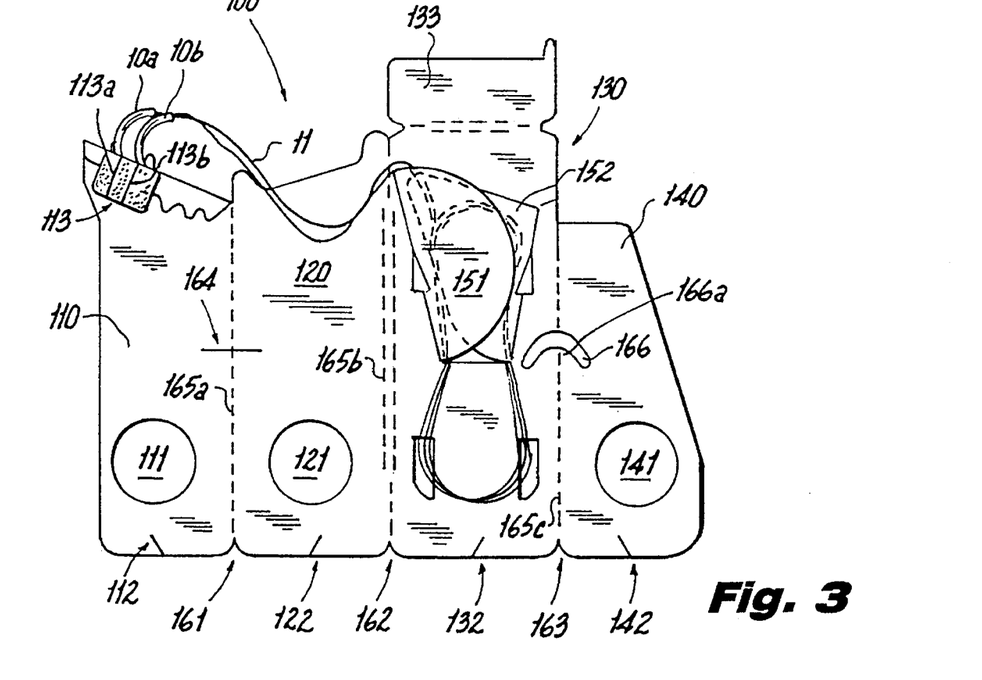
FIG. 3 is a plan view of the unfolded suture retainer of FIG. 2 with a double-armed suture retained thereon.

After the suture is wound, the mounting pins are withdrawn, leaving a suture coil. Wing 152 is first folded over the suture coil, then wing 151 is folded over wing 152. Because of the angle of the fold lines 154a and 154b, the suture is guided into an "hourglass", or epitrochoid shape having contraposed incurvations on each of the two elongate sides, but without a crossover point. When the suture is withdrawn for use by a surgeon, the suture pulls out gradually. Insert 150 provides sufficient friction on the suture coil and prevents the entire coil from being pulled out at once. By providing wing 152 with an extended corner 152a, the suture will slide across the inside of wing 152 without significant contact with the intersection of wings 151 and 152. This configuration is preferred in order to decrease resistance upon withdrawal and to decrease the possibility of entanglement.

After the suture is loaded, suture retainer 100 is folded closed. Preferably, panel 140 is folded over panel 130, panel 110 is folded over panel 120 and set of panels 110 and 120 are folded over panels 130 and 140. Flap 133 is folded down, and the locking mechanisms are engaged to lock the suture retainer in a closed position. The suture retainer can then be inserted into a package and sterilized, after which the package is hermetically sealed. Referring to FIG. 6, to use suture retainer 100, the surgeon opens the external envelope (not shown), removes suture retainer 100, lifts up flap 133, and removes the needle(s) 10a, 10b from the park 113. Suture 11 can then be easily withdrawn from the retainer.

Figure 7:
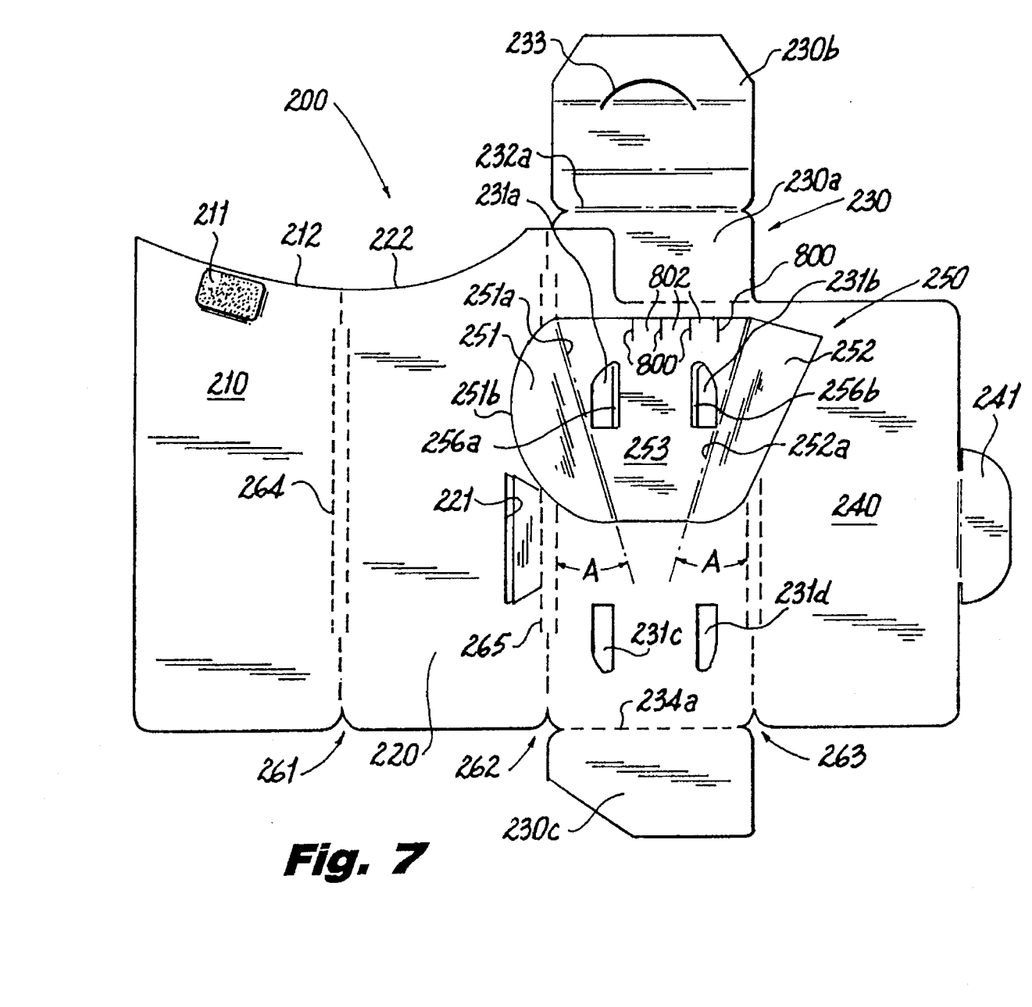
FIG. 7 is a plan view of an unfolded alternative embodiment of a suture package with insert.
Figure 8:
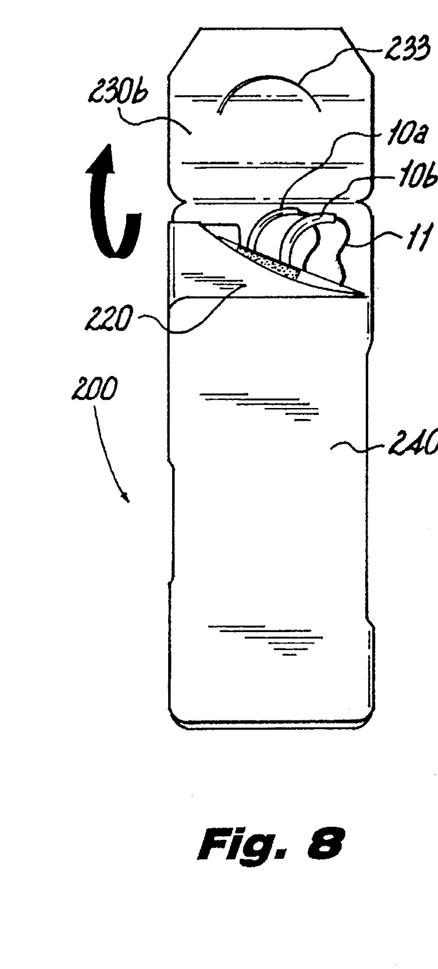
FIG. 8 is a plan view showing the suture retainer of FIG. 7 folded with a double-armed suture retained therein.
Figure 9:
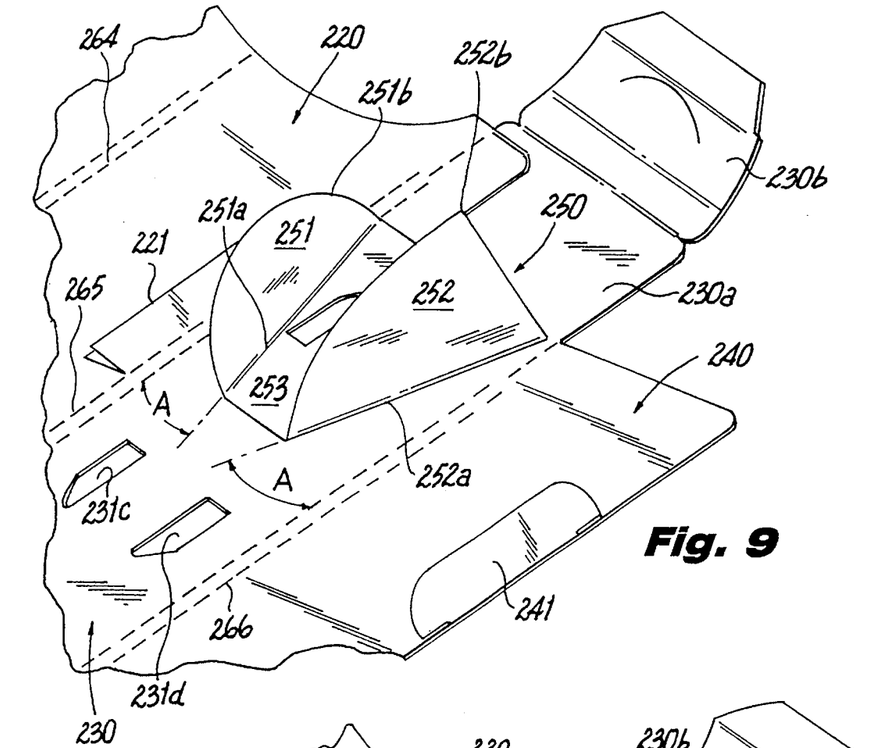
FIGS. 9 and 10 are perspective views showing alternative embodiments of the insert.

Referring now to FIGS. 7 to 9, an alternate embodiment of a suture retainer is shown. Suture retainer 200 includes needle retaining first panel 210 having needle retaining tab 211 which serves as a needle park. First panel 210 is foldably connected to a front cover panel, i.e. second panel 220 along gusset 264. Second panel 220 includes a vertical (as shown) elongated slot 221 which is adapted to receive a locking tab (explained below). The top edges 212 and 222 of panels 210 and 220, respectively, form a continuous arcuate edge.

A third panel 230 includes a main body portion 230a, a top foldover flap 230b and a bottom foldover flap 230c, and is foldably connected to the second panel 220 along fold line 265. Third panel 230 includes apertures 231a, 231b, 231c, and 231d for permitting loading pins to pass therethrough. Upper flap 230b is foldably connected to main body portion 230a at fold line 232a, and includes an arcuate shaped slot 233. Bottom foldover flap 230c is foldably connected to main body portion 230a at fold line 234a.

Insert 250 is preferably adhesively mounted to third panel 230 and includes center section 253, a first wing 251 foldably connected to center section 253 at an angled fold line 251a and a second wing 252 foldably connected to center panel 253 at angled fold line 252a. The angle A of the fold lines is as discussed above in connection with the previously described embodiment. Also, wings 251 and 252 provide spaced apart suture abutment surfaces generally facing each other in non-parallel relationship for contacting the outside of the suture loop. Wing 251 has a rounded edge 251b whereas wing 252 has a pointed edge 252b. As with the previously described embodiment insert 153 is preferably fabricated from TYVEK® type material. Also shown is optional needle holding structure that is formed by longitudinal adhesion lines 800 which create needle pockets 802 therebetween. Tips of needles (not shown) can be inserted between panel 230 and insert 250 and held in place by pockets 802.

The suture is loaded onto the third panel 230 in a manner similar to that presented with respect to the above described embodiment. Loading pins are disposed through the loading pin apertures (231a, 231b, 231c, and 231d in panel 230 and 256a and 256b in insert 250), the suture is loaded in a single loop configuration (i.e., circular or oval as opposed to a lemniscate ("figure 8") configuration, then the loading pins are withdrawn. Alternatively, insert flaps 251 and 250 can be partially folded while the loading pins are still up. Flaps 251 and 250 can then be folded completely as the loading pins are withdrawn. The insert is then folded over the suture, wing 252 being folded over the first, then wing 251 being folded over wing 252. The wings thus folded bias the suture loop to an epitrochoid ("hourglass") configuration having incurvate sides. The bottom flap 230c is then folded over to retain the bottom edge of the suture loop.

Fourth panel 240 is foldably connected to third panel 230 at fold line 266 and further includes a locking tab 241. Locking tab 241 is insertable into the slot 221 formed in panel 220. when the suture retainer 200 is folded, needle retaining panel 210 is first folded over panel 220. Panels 210 and 220 are then folded over panel 230. Fourth panel 240 is a front panel and folds over panels 210 and 220. Tab 241 is then tucked into slot 221 to keep the retainer closed. Upper foldover flap 230b is then folded over to cover the needles 10a and 10b. The suture retainer also includes indentations 261, 262, and 263 at the bottom of fold lines 264, 265, and 266, respectively.

Figure 10:
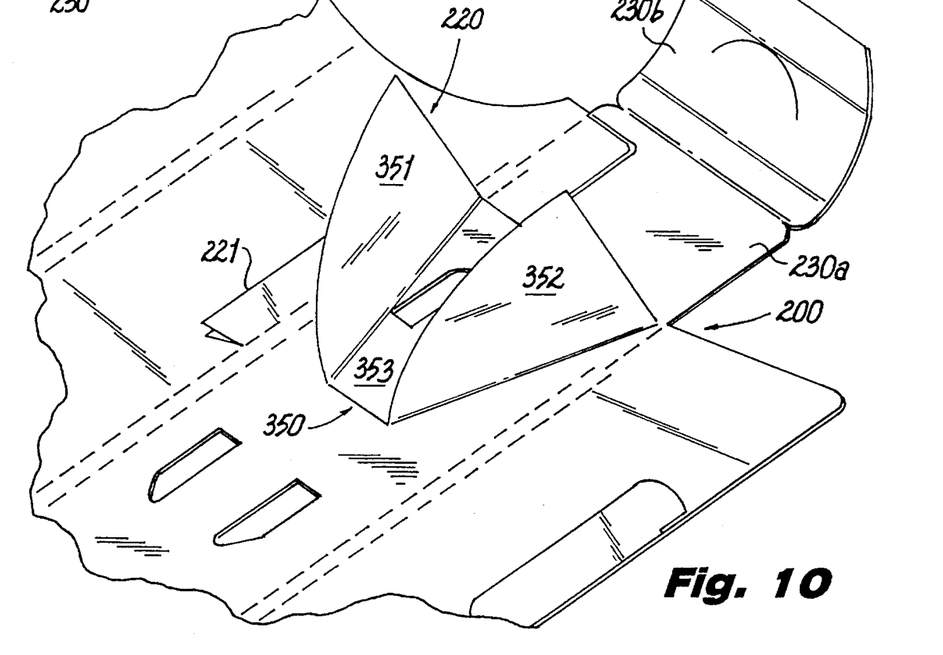

FIG. 10 illustrates another alternative embodiment of an insert. Insert 350 has two wings 351 and 352, each having a pointed edge 351a and 352a, respectively.

Figure 11:
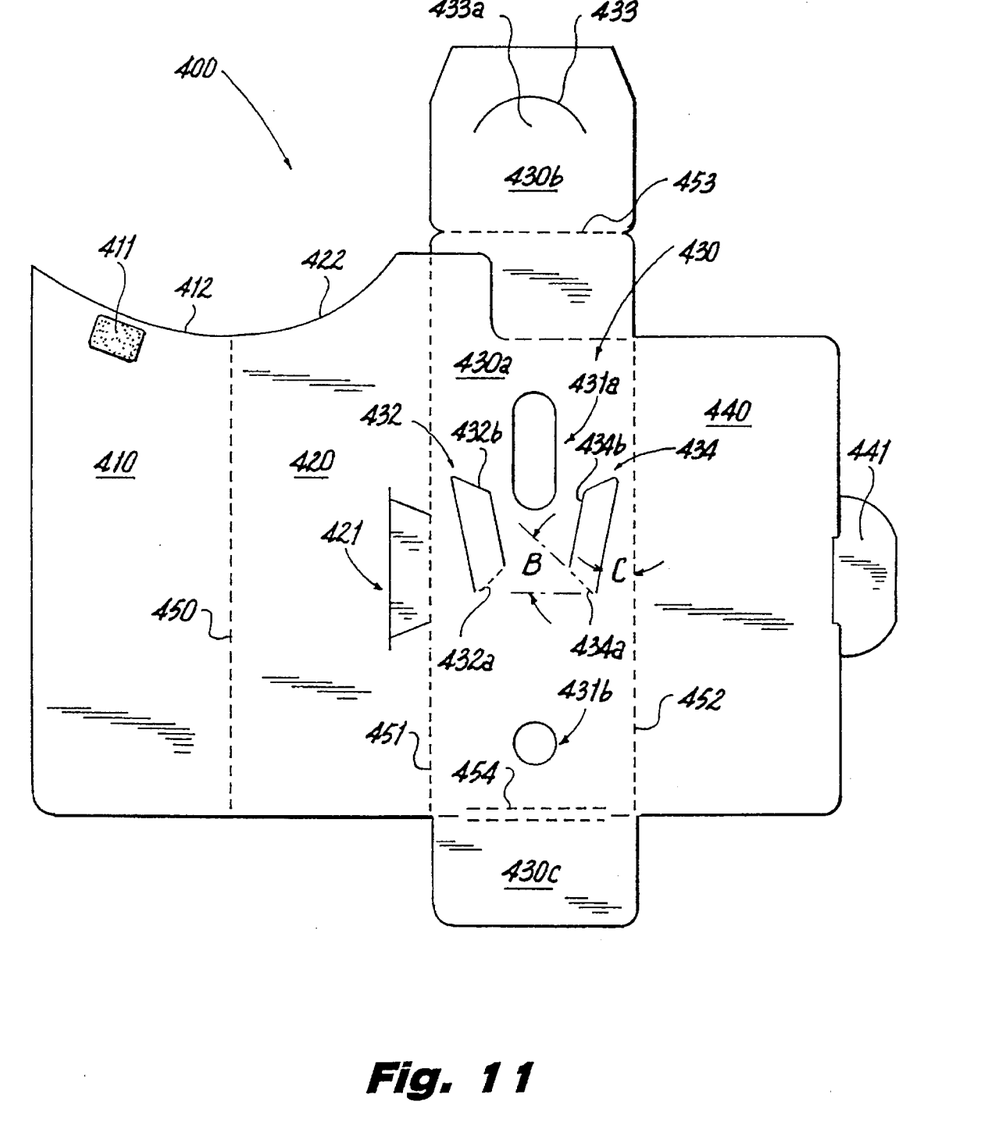
FIG. 11 is a plan view of another embodiment of the suture retainer, wherein tabs are used for maintaining the suture in an hourglass configuration.
Figure 12:
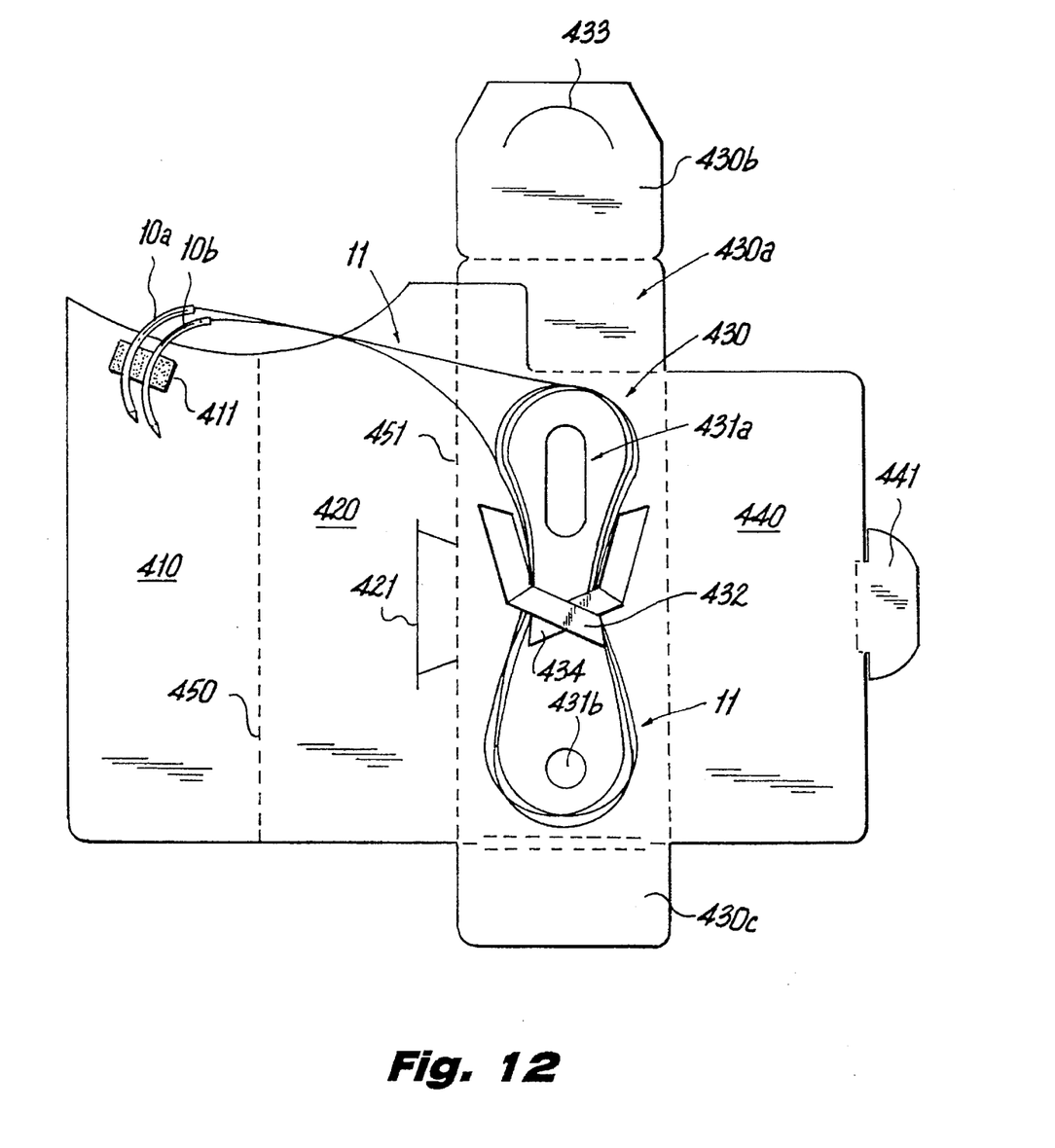
FIG. 12 is a plan view of the embodiment shown in FIG. 11 with a suture retained thereon.

FIGS. 11 and 12 illustrate another preferred, alternate embodiment for retaining a suture in an hourglass configuration. Suture package 400 includes a needle retaining first panel 410 having needle retaining tab 411. First panel 410 is foldably connected to a front cover panel, i.e. second panel 420, along fold line 450. Second panel 420 includes an elongated slot 421 which is adapted to receive a locking tab (explained below). The top edges 412 and 422 of panels 410 and 420, respectively, form a continuous arcuate edge.

Suture retaining third panel 430 includes main body portion 430a, top foldover flap 430b, and bottom foldover flap 430c, and is foldably connected to second panel 420 along fold line 451. Third panel 430 includes apertures 431a and 431b for permitting loading pins to pass therethrough. Aperture 431 is elongated in the vertical (as shown) direction to permit adjustment of the distance between the loading pins by movement of the loading pin disposed through aperture 431a towards or away from the loading pin disposed through circular aperture 431b.

Upper flap 430b is foldably connected to main body portion 430a at fold line 453 and includes an arcuate shaped slot 433, which defines a locking tab 433a. Bottom foldover flap 430c is foldably connected to main body portion 430a at gusset 454.

Unlike the previously described embodiments, suture package 400 does not have a separate insert for shaping the suture loop affixed thereto. Rather, the structure for biasing the suture loop to the hourglass shape includes two tabs 432 and 434, respectively, which are formed from the panel sheet 430a itself by cuts 432b and 434b, respectively. Tabs 432 and 434 are foldable at fold lines 432a and 434a, respectively, and are inclined inward from vertical fold lines 451 and 452, at an angle C where C ranges from 1° to 10°, and is preferably about 5°. Fold lines 432a and 434a are inclined from the horizontal (as shown) at an angle B where B ranges from 40° to 60°, preferably 45°–55°, and more preferably about 50°. Tabs 432 and 434 provide spaced apart suture abutment surfaces generally facing each other in non-parallel relationship for contacting the outside of the suture loop. Tabs 432 and 434 are preferably folded in a manner to prevent "catch points" that may snag an exiting suture.

Referring to FIG. 12, a double armed suture 11 is loaded onto third panel 430 with needles 10a and 10b mounted onto foam tab needle park 411. Tabs 434 and 432 are folded down over and across the suture loop to bias it into the hourglass shape. After the suture is fully mounted, flap 437 is folded over to retain the bottom of the suture loop 11.

Referring again to FIG. 11, fourth panel 440 is foldably connected to third panel 430 at fold line 452 and has a locking tab 441 which is insertable into slot 421 formed in panel 420. When the suture retainer 400 is folded, needle retaining panel 410 is preferably first folded over panel 420. Panels 410 and 420 are then folded over panel 430 such that panel 420 is on top. Panel 440 is then folded over panel 420 and tab 441 is tucked into slot 421 to keep the suture retainer closed.

Figure 17:
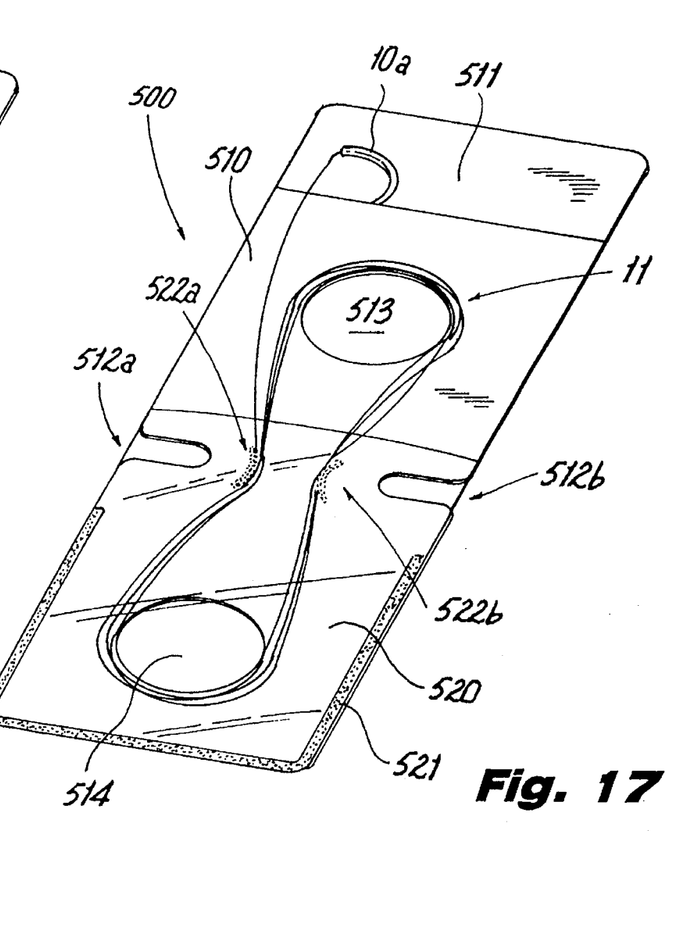

Referring now to FIG. 17, another embodiment of a suture retainer capable of retaining a suture in an hourglass configuration is shown. Suture retainer 500 includes a base panel 510 having needle park 511, and two loading pin apertures 513 and 514. The base panel may be fabricated from any suitable material such as paper stock, Tyvek® brand spun bonded polyolefin fiber sheet, plastic, or any other suitable material. Base panel 510 also includes side slots 512a and 512b. A cover sheet 520 of preferably transparent material is bonded to the bottom portion (as shown) of the base panel 510 at bonding lines 521 and 522a and 522b. The cover sheet 520 is preferably a clear plastic film and is bonded to the base panel 510 by any suitable procedure known in the art, such as adhesive bonding, heat welding, etc. Bonding line 521 extends around the periphery of the bottom portion of the cover sheet 520 and base panel 510, but an unsealed portion of the edge remains in the vicinity of the slots 512a and 512b for reasons discussed below. The two crescent shaped bonding lines or areas 522a and 522b provide structure for holding the suture loop 11 in an epitrochoidal or hourglass shape. Suture package 500 is shown in conjunction with a single armed suture 11 having needle 10a attached thereto. Unarmed and double armed sutures can also be mounted in suture package 500.

Figures 13, 14, 15:
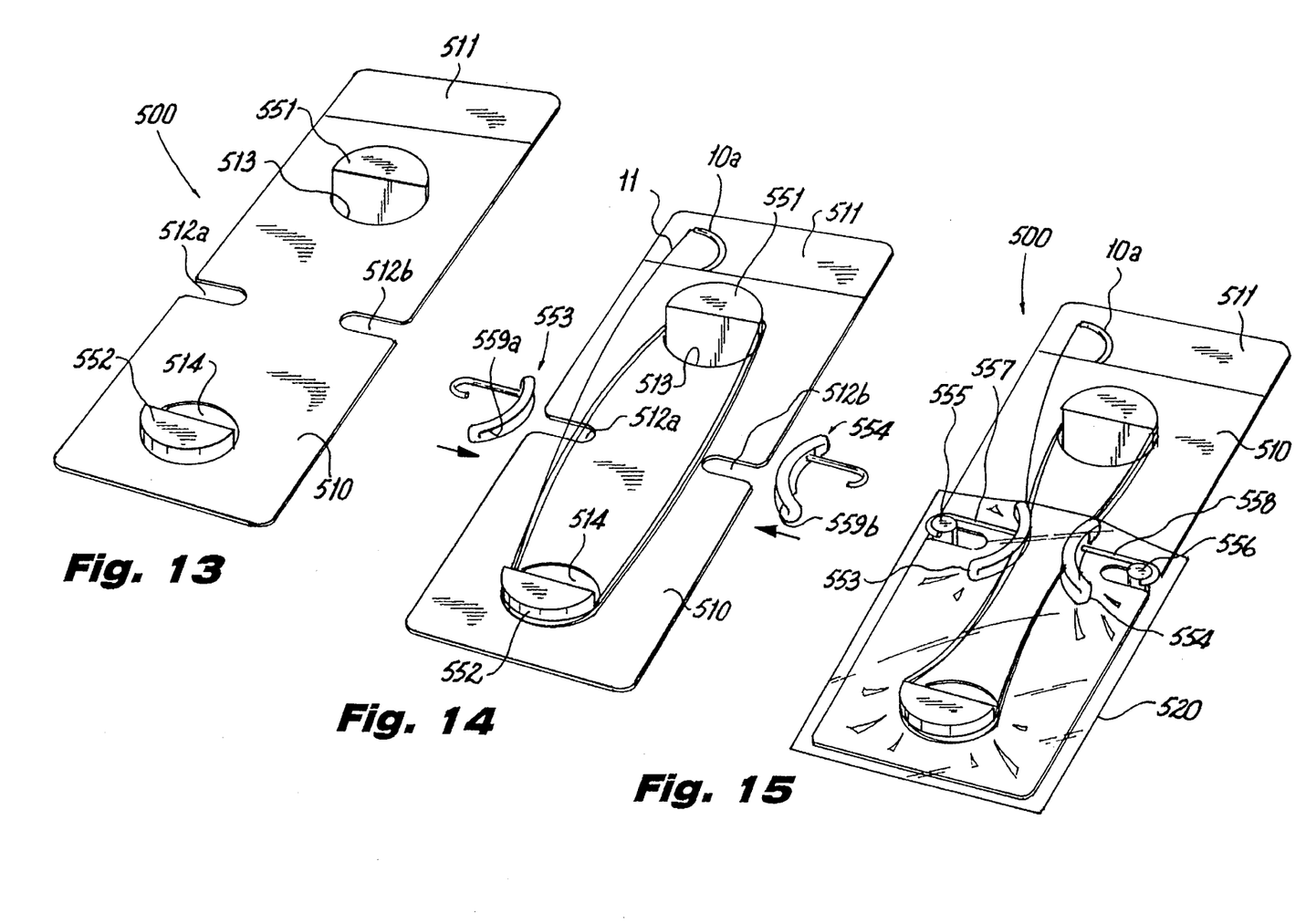
FIGS. 13–17 are perspective sequential views showing yet another embodiment of the suture retainer and a method for maintaining a suture therein in an hourglass configuration.

FIGS. 13 to 16 illustrate a procedure for loading the suture material suture package 500. FIG. 13 illustrates base panel 510 with hemispherical loading pins 551 and 552 disposed through circular loading pin apertures 513 and 514, respectively. In the next step, shown in FIG. 14, suture 11 (with needle 10a) is wound around the loading pins to form an oval loop. Crescent shaped plows 553 and 554 are positioned alongside the base panel 510 in the vicinity of slots 512a and 512b. The plows are oriented such that the convex sides face inwardly towards each other. The concave sides face outwardly. Each plow has a trough 559a and 559b, respectively, for engaging the suture strands.

Plows 553 and 554 are attached to respective posts 555 and 556 by connecting shafts 557 and 558, respectively. Posts 555 and 556 are movable into the slots 512a and 512b, respectively, to position the plows 553 and 554 for contacting the suture loop 11. As shown in FIG. 15, plows 553 and 554 are moved laterally inward, thereby biasing the suture loop 11 into an hourglass shape. Next, clear plastic cover sheet 520 is positioned on top of the bottom portion of the base panel 510. Of course, the plows can move into slots 512a and 512b after sheet 520 is positioned over panel 510.

Figure 16:
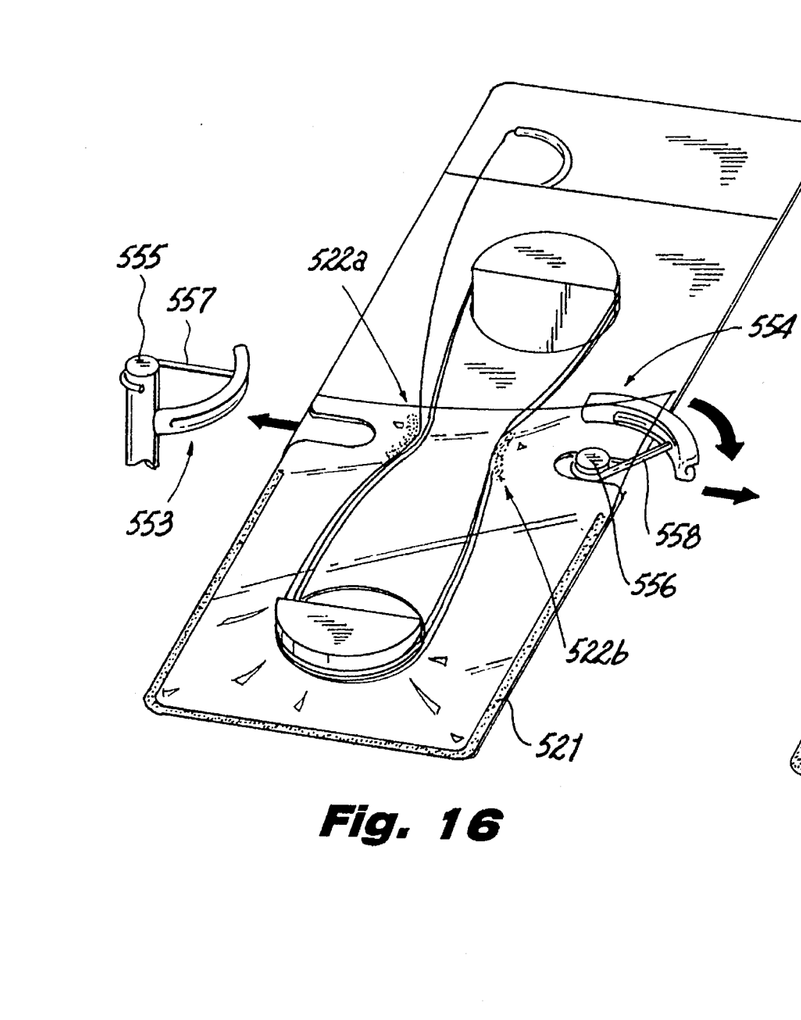

As shown in FIG. 16, the cover sheet 520 is welded to the base panel 510 around periphery 521 and, along the concave sides of the plows to form crescent shaped welds 522a and 522b. Crescent shaped welds 522a and 522b provide spaced apart suture abutment surfaces generally facing each other and in non-parallel relationship for contacting the outside of the suture loop. Excess overlap of the cover sheet 520 can be trimmed. The plows are disengaged by rotation and/or lateral outward movement of the posts 555 and 556, which is permitted because the peripheral weld 521 does not extend to the area of slots 512a and 512b. Finally, the loading pins 551 and 552 are withdrawn leaving the finished suture package 500 with mounted suture 11 as shown in FIG. 17.

While the above description contains many specifics, these specifics should not be construed as limitations on the scope of the invention, but merely as exemplifications of preferred embodiments thereof. Those skilled in the art will envision many other possible variations to create suture retainers for maintaining a suture in an hourglass or epitrochoidal configuration that are within the scope and spirit of the invention as defined by the claims appended hereto.

As defined in the claims, "retention means" refers to inserts 150, 250 or 250, tabs 432 and 434, or to welds 522a and 522b, and their equivalents.

As defined in the claims, "locking means" refers to either parts 164 and 166, parts 112, 122, 132 and 142, or parts 221 and 241.

What is claimed is:

1. A surgical suture retainer comprising retention means for retaining a suture loop in a generally epitrochoidal shape, said retention means having at least two spaced apart suture abutment surfaces generally facing each other in non-parallel relationship for contacting the outside of the suture loop.

2. The retainer of claim 1 wherein the retainer is a plurality of foldably connected panels.

3. The retainer of claim 2 wherein the retention means is an insert member mounted to one of the panels.

4. The retainer of claim 3, wherein the insert member is fabricated from a sheet comprising spunbonded polyolefin fibers.

5. The retainer of claim 2 wherein the retention means are first and second tabs, each bounded by at least one cut line and a fold line in one of the panels, the first and second tabs being foldable along their respective fold lines.

6. The retainer of claim 1 wherein the retainer comprises at least one panel and a cover sheet attached thereto by joining at predetermined bonding joint locations.

7. The retainer of claim 6 wherein the retention means are first and second bonding areas configured and positioned to retain, a suture loop in an epitrochoidal shape.

8. The retainer of claim 7 wherein the first and second bonding areas are each crescent shaped and oriented with convex sides inwardly facing each other.

9. A surgical suture retainer comprising retention means for retaining a suture loop in a generally epitrochoidal shape, wherein the retainer is a plurality of foldably connected panels and the retention means is an insert member mounted to one of the panels, and wherein the insert member has a center portion attached to one of the panels and first and second wings foldably connected to the center portion along respective fold lines, the first and second wings being foldable over the center portion to form a suture retaining pocket.

10. The retainer of claim 9, wherein the fold lines are inwardly inclined towards each other so as to form a generally V-shaped boundary.

11. The retainer of claim 10, wherein the fold lines define an angle of from about 5° to about 45°.

12. A surgical suture retainer comprising retention means for retaining a suture loop in a generally epitrochoidal shape, wherein the retainer is a plurality of foldably connected panels, and wherein the retention means are first and second tabs, each bounded by at least one cut line and a fold line in one of the panels, the first and second tabs being foldable along their respective fold lines, and wherein one of the panels is elongated so as to define a lengthwise direction in the direction of elongation, and each tab is elongated and oriented at an angle of from 1 degree to 10 degrees with respect to the lengthwise direction of the panel.

13. The retainer of claim 12, wherein the one of the panels has a lateral direction orthogonal to the lengthwise direction, and the fold lines of the tabs are respectively oriented at an angle of from about 40 degrees to about 60 degrees with respect to the lateral direction.

14. A suture retainer for retaining a suture loop in a generally epitrochoidal shape comprising:

a first panel;

a second panel foldably connected to the first panel along a first panel fold line;

a third panel foldably connected to the second panel along a second panel fold line;

an insert member mounted to the third panel, the insert member having a center portion fixedly bonded to the third panel and said insert member having at least two spaced apart suture abutment surfaces generally facing each other for contacting the outside of the suture loop, and a fourth panel foldably connected to the third panel along a third panel fold line.

15. The retainer of claim 14, wherein the insert member has first and second wings foldably attached to the center portion along respective insert fold lines.

16. The retainer of claim 15, wherein the first wing has an arcuate edge and the second wing has an edge with an angled corner.

17. The retainer of claim 14, wherein the insert is fabricated from a sheet comprising spunbonded polyolefin fibers.

18. The retainer of claim 14, wherein the first, second and fourth panels each have an aperture, the apertures being alignable upon folding of the retainer to permit fluid to access a suture through the folded retainer.

19. The retainer of claim 14, wherein the third panel has a plurality of apertures for permitting passage therethrough of loading pins.

20. The retainer of claim 14, further comprising locking means for locking the retainer in a closed configuration.

21. The retainer of claim 20, wherein the locking means is a tab defined by a slot extending across the third and fourth panels, and a lateral slit extending across the first and second panels, the tab being engageable with the slit when the retainer is in a folded configuration.

22. The retainer of claim 20, wherein the locking means is an angled slit positioned on a bottom edge of each of the first, second, third, and fourth panels, each slit defining a tab, the tabs of the third and fourth panels being insertable through the slits of the first and second panels, and the tabs of the first and second panels being insertable through the slits of the third and fourth panels, when the retainer is in a folded configuration.

23. The retainer of claim 14, further comprising a surgical suture at least partially retained on the third panel in the form of a coil having a plurality of turns wound in a single loop.

24. The retainer of claim 23, wherein the loop has an hourglass configuration.

25. The retainer of claim 23, wherein the suture is a monofilament suture.

26. The retainer of claim 23, wherein the suture is a multifilament suture.

27. The retainer of claim 14, wherein needle holding pockets are formed between the insert member and third panel.

28. A suture retainer comprising:

a first panel;

a second panel foldably connected to the first panel along a first panel fold line;

a third panel foldably connected to the second panel along a second panel fold line;

an insert member mounted to the third panel, the insert member having a center portion fixedly bonded to the third panel, and a fourth panel foldably connected to the third panel along a third panel fold line, wherein the insert member has first and second wings foldably attached to the center portion along respective insert fold lines, and wherein the insert fold lines are inwardly inclined towards each other so as to form a generally V-shaped boundary.

29. The retainer of claim 28, wherein the insert fold lines define an angle of from about 5° to about 45°.

30. In combination, a suture retainer and a coiled suture, the suture retainer comprising a plurality of foldably connected panels and an insert member mounted to one of the panels, wherein the coiled suture is at least partially disposed adjacent the insert member and the insert member retains the coiled suture in a generally epitrochoidal shape, said insert member having at least two non-parallel surfaces in spaced apart generally facing relationship to each other.

31. In combination, a suture retainer and a coiled suture, the suture retainer comprising retention means abutting the outer edge of the coiled suture at two spaced apart positions for holding the coiled suture in a generally epitrochoidal shape, said retention means including two spaced apart non-parallel surfaces in generally facing relationship.

* * * * *